Figure 1:
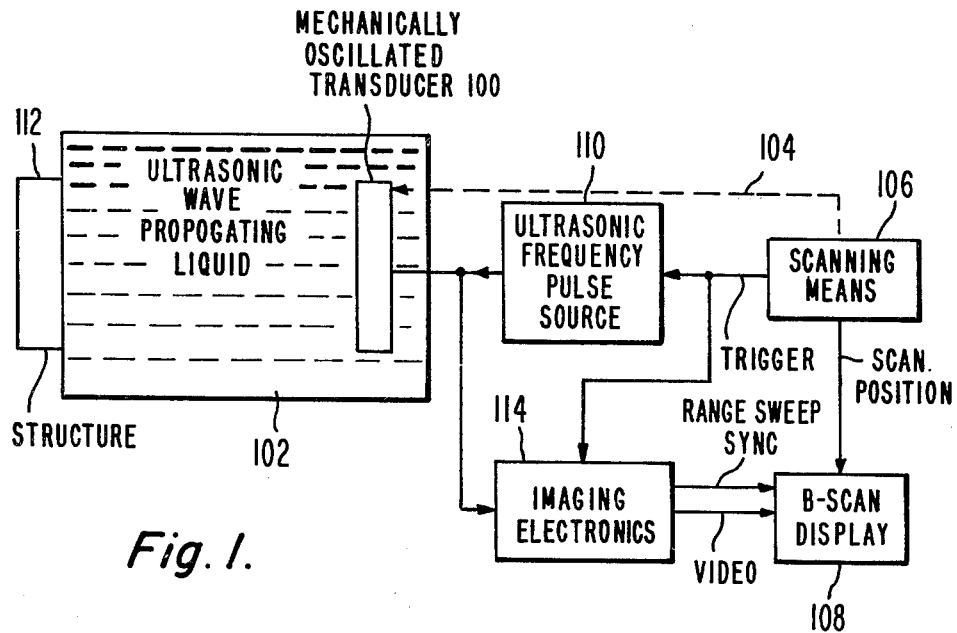

United States Patent [19]

Vilkomerson et al.

[11] 4,197,751
[45] Apr. 15, 1980

[54] PULSE-ECHO ULTRASONIC WAVE-ENERGY IMAGING SYSTEM INCORPORATING HIGH-ANGULAR VELOCITY OSCILLATED TRANSDUCER

[75] Inventors: David H. R. Vilkomerson, Princeton; Reuben S. Mezrich, Rocky Hill, both of N.J.

[73] Assignee: RCA Corporation, New York, N.Y.

[21] Appl. No.: 964,898

[22] Filed: Dec. 5, 1978

[30] Foreign Application Priority Data

Dec. 12, 1977 [GB] United Kingdom ............... 51684/77
Dec. 12, 1977 [GB] United Kingdom ............... 51685/77
Dec. 12, 1977 [GB] United Kingdom ............... 51686/77

[51] Int. Cl.² ............................................. G01N 29/04
[52] U.S. Cl. ....................................................... 73/633
[58] Field of Search ................. 73/621, 620, 618, 633; 128/2 V, 660

[56] References Cited

U.S. PATENT DOCUMENTS

| 3,159,023 | 12/1964 | Steinbrecher | 73/633 |
| 3,248,726 | 4/1966 | Sonnenfeldt | 340/347 P |
| 3,741,004 | 6/1973 | Posakony | 73/620 |
| 3,752,255 | 8/1973 | Hill et al. | 73/633 |

FOREIGN PATENT DOCUMENTS 1085624 4/1955 France ....................................... 73/633

Primary Examiner—Anthony V. Ciarlante
Attorney, Agent, or Firm—George J. Seligsohn; Samuel Cohen

[57] ABSTRACT

Transducer completely immersed in ultrasonic propagating liquid can be oscillated back and forth at a high rate, without producing significant turbulence in liquid, if oscillation velocity varies as a predetermined smooth continuous function of time.

9 Claims, 6 Drawing Figures

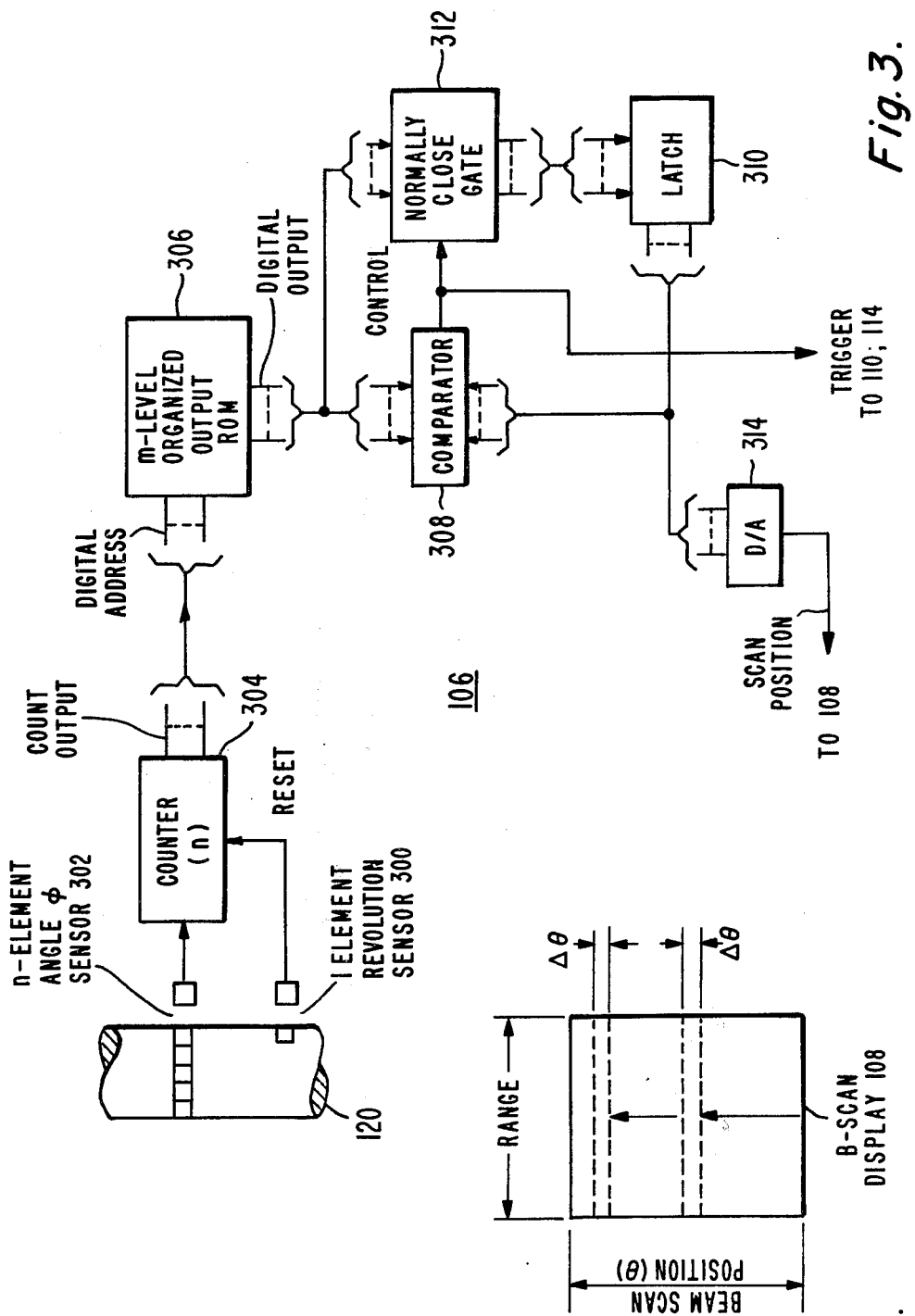

PULSE-ECHO ULTRASONIC WAVE-ENERGY IMAGING SYSTEM INCORPORATING HIGH-ANGULAR VELOCITY OSCILLATED TRANSDUCER

This invention relates to beam scanning means for a pulse-echo ultrasonic wave energy imaging system and, more particularly, to a technique for scanning back and forth a structure to be insonified at a high rate with a beam of ultrasonic wave energy derived from a mechanically oscillated electro-acoustic transducer immersed in a propagating liquid.

Pulse-echo ultrasonic wave energy imaging systems for displaying an image of insonified structure on a cathode-ray-tube display (CRT), such as a B-scan or C display, are known in the art. These systems employ an electro-acoustic transducer immersed in a liquid propagating medium, such as water, for generating a pulse beam of ultrasonic wave energy that is propagated through the liquid to a remotely-located structure to be insonified. The beam may be a pencil beam, or alternatively, may be a large-aperture beam that is focused to a small cross section within the insonified structure. In any case, scanning means are provided for scanning the beam with respect to the structure to be imaged. Reflected echoes from the insonified structure are propagated through the liquid back to the transducer, where they are detected as electrical signals. The detected signals, after passing through imaging electronics (in which they may be amplified, range-gated or otherwise processed), are used to intensity modulate the electron beam of a CRT. In a B-scan display, a scan position signal from the scanning means deflects the electron beam of the CRT in correspondence with the ultrasonic beam scan position. At the same time, successive range sweeps occurring in synchronized time relationship with pulses or ultrasonic wave energy launched from the transducer that correspond to the depth dimension of the insonified structure, deflect the electron beam of the CRT in the beam scan direction. In a B-scan, there may be as many as several hundred range sweeps per scan cycle, and there may be as many as several hundred scan cycles per minute. In a C-scan, both the ultrasonic beam and the CRT electron beam are scanned in two dimensions. The scan rate in a first of these two dimensions is relatively high (e.g. 100 or more cycles per minute), while the scan rate in a second of these two dimensions is relatively slow (e.g. 20 or fewer cycles per minute).

Scanning of a beam of ultrasonic wave energy by mechanical means requires that the scanning means includes at least one movable member immersed in the ultrasonic propagating liquid. Proper acoustic characteristics of the propagating liquid require that any turbulence of the propagating liquid caused by movement of the immersed movable member be insignificant. A revolving member, revolving at a uniform angular velocity, produces insignificant turbulence even at the high scan rate employed for B-scan or for the first dimension of C-scan. Also, an oscillating movable member immersed in a propagating liquid produces insignificant turbulence if the rate of oscillation is sufficiently slow (as it is for a C-scan in the second dimension). However, in the past, it was believed that an immersed movable member in an ultrasonic wave energy propagating liquid would necessarily produce an intolerable level of turbulence when oscillated back and forth at a rate of one-hundred or more cycles per minute. For this reason the prior art employs immersed revolving means, such as a pair of Risley prisms counter-rotating at a high uniform rate (e.g. in the range of 100-1500 revolutions per minute) to mechanically achieve back and forth oscillation of the ultrasonic beam at the high rate (e.g. 100-1500 cycles per minute) requires for a B-scan or the fast scan of a C-scan image display.

In accordance with the present invention, it has been found that an electro-acoustic transducer completely immersed in the propagating liquid of a pulse-echo ultrasonic wave energy imaging system can be cyclically oscillated back and forth at a repetition rate of at least 100 cycles per minute about a given axis of the transducer, between respective first and second angular limits, without causing any significant turbulence in the propagating liquid, if the transducer oscillates with a velocity that varies as a predetermined smooth continuous function of time.

Figure 1A:
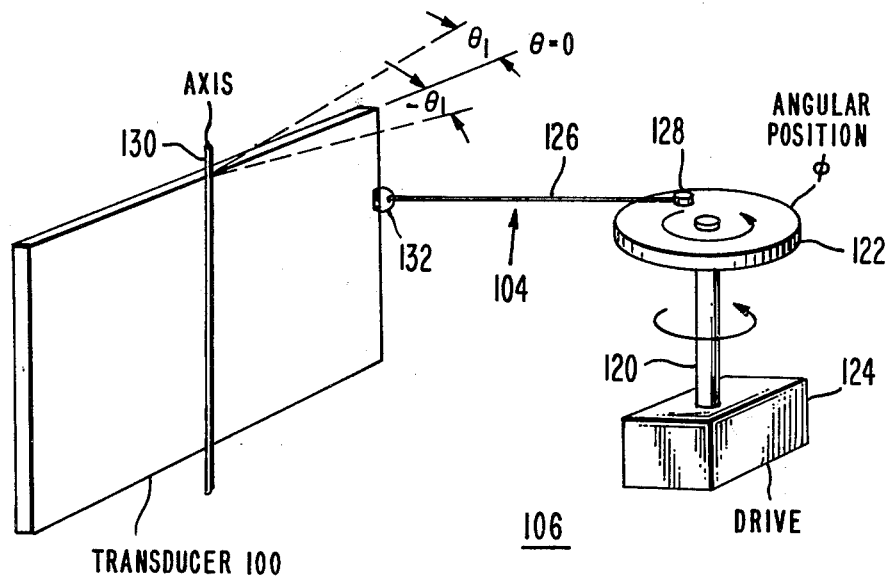
Figure 1B:
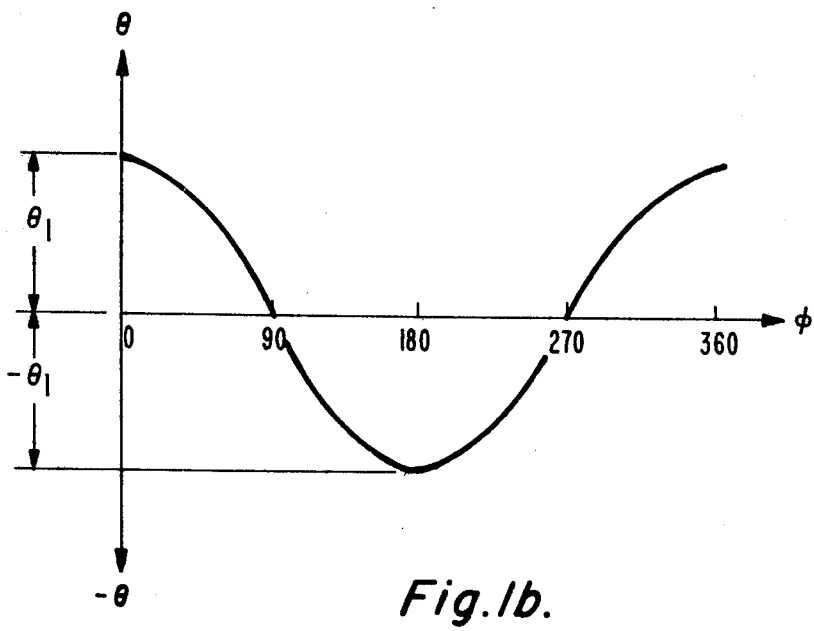
Figure 2A:
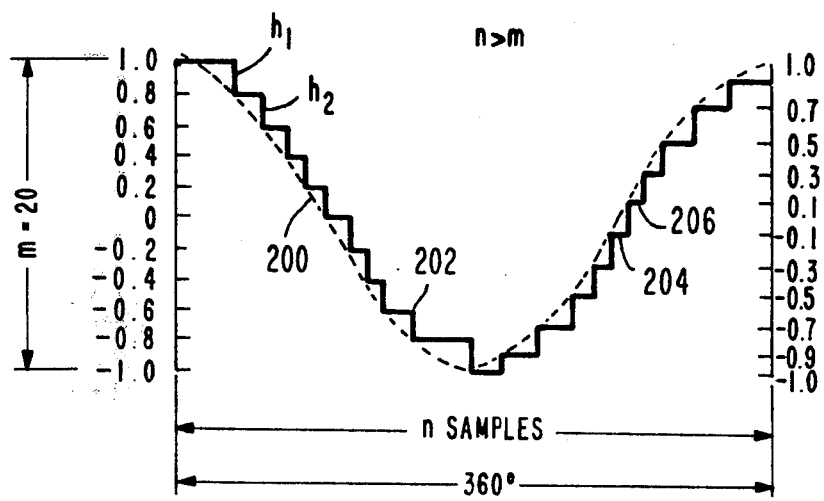

In the drawings:

FIG. 1 is a block diagram of a pulse-echo ultrasonic wave energy imaging system incorporating the present invention;

FIG. 1a schematically illustrates the linkage between the mechanically-oscillated transducer and the mechanical portion of the scanning beams of FIG. 1;

FIG. 1b is a cosine waveform, corresponding to the angular scan position as a function of time, of the oscillated transducer of FIG. 1, during each complete cycle of oscillation;

FIG. 2 diagramatically illustrates the display raster of the B-scan display of FIG. 1;

FIG. 2a is a graph of the histogram waveform of the scan position (vertical deflection) signal applied to the B-scan display, and FIG. 3 is a block diagram of an embodiment of the electronic portion of the scanning means of FIG. 1, for deriving the scan position signal for the B-scan display.

Referring to FIG. 1, mechanically-oscillated electro-acoustic transducer 100 is completely immersed in ultrasonic wave propagating liquid 102, which may be water. As indicated by dashed line 104, transducer 100 is mechanically linked to scanning means 106. Scanning means 106 includes a mechanical portion, which, together with linkage 104 and transducer 100, are shown in detail in FIG. 1a which is discussed below. Scanning means 106 further includes an electronic portion, shown in FIG. 3, which derives a trigger pulse and a scan-position signal. The scan position signal is applied to the vertical deflection circuit of B-scan display 108. In addition, the trigger pulse output from scanning means 106 is applied as an input to ultrasonic frequency (UF) pulse source 110, which energizes transducer 100 with a UF pulse (i.e., a frequency in the range of 1.0–10 MHz) in response to each trigger applied thereto. This results in a pulsed beam of ultrasonic wave energy being generated by transducer 100. The ultrasonic wave energy is propagated through liquid 102 to insonify structure 112. Structure 112 (which may be a portion of the human body) returns ultrasonic wave energy echoes to transducer 100, where they are detected as electrical signals. The detected signals are applied through imaging electronics 114 to an intensity-modulating electrode of B-scan display 108.

Referring to FIG. 1a, the mechanical portion of scanning means 106 comprises a revolving member consisting of shaft 120 and supporting wheel 122. This revolving member is revolved at a uniform angular velocity by drive 124. Linkage 104 comprises rod 106 having one end thereof coupled to wheel 122 at point 128 located near the periphery of wheel 122. Transducer 100 is rotatably mounted with respect to axis 130. The other end of rod 126 is coupled to one end of transducer 100 through universal joint 132.

During each revolution of the revolving member, the angular position $\phi$ of shaft 120, wheel 122 and, hence, point 128 varies linearly between 0° and 360°. Movement of point 128 imparts oscillating movement to transducer 100 through linkage 104. Specifically, during each revolution of point 128, transducer 100 is angularly rotated about axis 130 through one complete cycle of oscillation. During each cycle of oscillation, the angular position $\theta$ of transducer 100 varies from a first angular limit $\theta_1$ through zero to a second angular limit $-\theta_1$; and then back again through zero to the first angular limit $\theta_1$.

Although point 128 of the revolving member revolves at a uniform angular velocity (so that one complete revolution of point 128 is equal to one complete oscillation cycle of transducer 100), the angular velocity and rotation of transducer 100 is non-uniform. More particularly, as shown in FIG. 1b, the waveform derived by plotting the angular position $\theta$ of oscillating transducer 100 as a function of the angular position $\phi$ of the revolving member (i.e. point 128) is a cosine. As is known, a cosine waveform is a non-linear continuous periodic function. Therefore, unlike a linear function (such as a sawtooth wave or other type of triangular periodic wave), there are no discontinuities in a cosine waveform. In particular, at angular limits $\theta_1$ and $-\theta_1$, where the direction of movement of oscillating transducer 100 reverses, the slope of the cosine waveform is zero (i.e. the velocity is zero). It is for this reason that oscillating transducer 100 does not produce any significant turbulence in propagating liquid 102, even when the rate of oscillation is high (e.g. a range of 100–1500 cycles per minute).

FIG. 2 shows the display raster of B-scan display 108. A linear range sweep in the horizontal direction of display 108 occurs in response to each range sweep sync pulse applied thereto from imaging electronics 114. As known in the art, imaging electronics 114 may include range gating means that derives a range sweep sync pulse that occurs a certain time delay subsequent to the occurrence of each trigger input to imaging electronics 114. Further, each trigger occurs in time coincidence with a UF pulse applied to transducer 100. The time interval of each range sweep on display 108 includes the time interval during which ultrasonic wave echoes returned from structure 112 are detected by transducer 100 and are applied as a range gated video signal input to B-scan display 108 through the then open range gate of imaging electronics 114.

The vertical position of each successive horizontal range sweep on display 108 depends upon the angular position $\theta$ of oscillated transducer 100 at that time. In order to provide the clearest display, it is essential that the scan position increment $\Delta\theta$ between any pair of successive range sweeps on display 108 be substantially constant over the whole display. However, the beam scan position $\theta$ does not vary linearly, but varies in accordance with the cosine function shown in FIG. 1b. Therefore, if the trigger pulses occurred at a substantially constant periodic rate (which is usual in B-scan displays), the value of $\Delta\theta$ would be too small at the top and at the bottom of each display and would be too large in the middle of each display. The reason for this can be seen from FIG. 1b. During the first-half of each cycle of oscillation of transducer 100, the slope of the cosine waveform increases from zero (at $\theta=\theta_1$) to a maximum slope (at $\theta=0$) and then decreases to a zero slope ($\theta=-\theta_1$). During this first-half cycle, the vertical deflection of display 108 is from top-to-bottom. During the second-half of a cycle of the cosine waveform, the slope increases from zero ($\theta=-\theta_1$) to a maximum slope ($\theta=0$) and then decreases to a zero slope ($\theta=\theta_1$). During the second-half cycle of a cosine waveform, the vertical deflection of display 108 is from bottom-to-top. Thus, during each complete scanning cycle, the beam scan occupies the same angular position $\theta$ twice, once on the way down from top-to-bottom and once on the way up from bottom-to-top.

It is desired that successive range sweeps occur at fixed predetermined angular increments of oscillated transducer 100. However, in order to prevent each of the respective range sweeps which occur during the bottm-to-top vertical deflection of display 108 from coinciding with a corresponding one of the respective range sweeps which occur during the top-to-bottom vertical deflection of display 108, the bottom-to-top range sweeps should be interlaced with the top-to-bottom range sweeps.

FIG. 2a shows in phantom cosine waveform 200 (which is identical to the cosine waveform shown in FIG. 1b) and also shows histogram 202 which closely conforms to cosine waveform 200. Histogram 202 divides each complete cycle (360°) of cosine waveform 200 into a first plural integer n of equal sampling time intervals. Cosine waveform 200 has a normalized positive peak amplitude of 1.0 and a normalized negative peak amplitude of $-1.0$. Histogram 202 divides the peak-to-peak amplitude interval between 1.0 and $-1.0$ into a second plural integer m of different, equally spaced, amplitude levels. The value of m is equal to the number of range sweeps within a display frame of B-scan display 108. In practice, the value of m is usually in the range of from 100 to 200, or even more. However, for illustrative purposes, the value of m shown in FIG. 2a is only 20. The group of 20 levels shown in FIG. 2a comprises a first sub-group of 10 amplitude levels, which occur during the first half-cycle of cosine waveform 200, and a second sub-group of 10 amplitude levels, which occur during the second half-cycle of cosine waveform 200. The first sub-group of 10 amplitude levels consists of 1.0, 0.8, 0.6, 0.4, 0.2, 0, $-0.2$, $-0.4$, $-0.6$ and $-0.8$. The second sub-group of 10 amplitude levels consists of $-1.0$, $-0.9$, $-0.7$, $-0.5$, $-0.3$, $-0.1$, 0.1, 0.3, 0.5, 0.7 and 0.9.

Histogram 202 maintains any one of the 20 amplitude levels until the occurrence of the particular one of the n sample time intervals at the end of which the amplitude of cosine waveform 200 falls or rises to the next amplitude level in the particular sub-group corresponding to the then-occurring half-cycle of waveform 200.

It can be seen from FIG. 2a that the duration of an amplitude level in the vicinity of the positive or negative peak amplitude (where the slope of a cosine waveform in small) is longer than the duration of an amplitude level in the vicinity of zero (where the slope of a cosine waveform is large). Each sampling time interval must have a smaller duration than that of a minimum-duration amplitude level (i.e., amplitude levels 204 and 206). Therefore, the value of the first plural number n is always substantially larger than that of the second plural number m. Preferably, in order to achieve a close fit between histogram 202 and cosine waveform 200, the duration of minimum-duration amplitude level 204 or 206 should be several times that of an individual sampling time interval. Further, while each different amplitude level of histogram 202 corresponds to a separate range sweep of B-scan display 108, the time of occurrence of each change in amplitude level (each vertical segment $h_1, h_2 \ldots$ ) of histogram 202 occurs in time synchronous relationship with a trigger applied to ultrasonic frequency pulse source 10 to effect the generation of a pulse of ultrasonic wave energy from transducer 100. Scanning means 106 includes an electronic portion for generating such triggers, in addition to deriving a scan position (vertical deflection) signal, having a waveform corresponding to histogram 202, for B-scan display 108.

Referring to FIG. 3, there is shown an illustrative embodiment of such an electronic portion of scanning means 106. As shown in FIG. 3, revolving shaft 120 of the mechanical portion of scanning means 106 (shown in detail in FIG. 1a) has associated therewith both 1-element revolution sensor 300 and n-element angle $\phi$ sensor 302. By way of example, sensor 300 may include a magnetic element in shaft 120 which passes a fixed coil once every revolution of shaft 120, for inducing a voltage pulse at the end of each revolution of shaft 120. Similarly, sensor 302 may include a group n magnetic elements spatially distributed at equal intervals about the circumference of revolving shaft 120, each of which induces a voltage pulse as it passes a fixed coil of sensor 302. (It is to be appreciated that alternatives such as optical coding and optical sensors may be used instead of the magnetic means shown).

During each revolution of shaft 120, the n pulses generated by sensor 302 are applied as an input to counter 304. The output from counter 304, which digitally manifests the count then registered in counter 304, forms a digital address to m-level organized output read-only-memory (ROM) 306. ROM 306 is organized to convert each and every successive digital address count having a value smaller than the count at which $h_1$ occurs (see FIG. 2a) into a digital output value manifesting 1.0. ROM 306 then converts each and every successive digital address count equal or greater than the count at which $h_1$ occurs but less than that at which $h_2$ occurs (FIG. 2a) into a digital output value manifesting 0.8. In a similar manner, ROM 306 converts all the rest of the n digital address counts into a corresponding digital output value manifesting the appropriate one of the m amplitude levels of histogram 302 shown FIG. 2a. Therefore, in effect, ROM 306 is a look-up table, for deriving in digital form each of the successive levels of a histogram of a predetermined (e.g. cosine) time-varying waveform.

Each digital output from ROM 306 is applied as a first digital input to comparator 308, while the digital output of any digital number then stored in latch 310 is applied as a second digital input to comparator 308. If the first and second digital inputs of comparator 308 manifest the same value, nothing happens. However, whenever the first and second digital inputs to comparator 308 manifest different values, comparator 308 produces a control pulse, which opens normally closed gate 312. With gate 312 open, the digital output from ROM 306 is forwarded as a digital input for storage in latch 310, where it replaces the formerly stored number. This results in first and second digital inputs to comparator 308 becoming again equal to each other, thereby closing gate 312. Digital-to-analog (D/A) 314 converts the digital value manifested by the output from latch 310 into the scan position deflection signal for B-scan display 108.

If, as has been assumed, ROM 306 is organized to provide a digital output corresponding to histogram 202, then the scan position signal from D/A 314 necessarily varies in time in accordance with histogram 202 and in synchronism with the angular position of oscillator transducer 100.

The present invention is not limited to use with a B-scan display. It may also be used with a C-scan display. In this latter case, oscillator transducer 100 is mounted in a gimbal, which is tiltable about an axis oriented perpendicular to axis 130 of transducer 100. For C-scan display, the rate of beam-scan oscillation about axis 130 may be quite fast (100 or more cycles per minute). However, the rate of tilting of the gimbal about the perpendicular axis is always slow, such as 10–20 revolutions per minute, (which produces negligible turbulence in the propagating liquid). Therefore, a rack and pinion may be employed to provide this slow tilt scan velocity, or, alternatively, an arrangement similar to that employed for the fast scan may be employed. In a C-scan the relatively fast beam scan position ($\theta$) of the display conventionally would be in the horizontal direction, while the slow linear tilt scan conventionally would be in the vertical direction.

Counter-rotating Risley prisms, discussed above, also produce a sinusoidal ultrasonic beam scan. Therefore, the electronic portion of scanning means 106, shown in FIG. 3, is equally applicable to a sinusoidal beam-scan produced by counter-rotating Risley prisms (or any other type of mechanical means).

Although it is preferred that scanning means 106 provide a sinusoidal oscillation of transducer 100, it is only essential for the purposes of this invention that the oscillation velocity be a smooth continuous function of time. Thus, for example, the oscillation velocity of transducer 100 could also vary as a cosine-square function, rather than as a cosine function.

What is claimed is:

1. In a pulse-echo ultrasonic wave energy imaging system comprising first means including an electroacoustic transducer for generating a scanning beam of pulsed ultrasonic wave energy that is propagated through a given liquid toward a remotely-located given structure to be insonified, said structure returning ultrasonic wave energy echoes propagated through said liquid to said transducer, wherein said transducer is completely immersed in said liquid and is rotatably mounted for angular movement about a given axis extending through said transducer, said given axis being oriented substantially normal to the direction of propagation of said scanning beam; the improvement:

wherein said first means includes second means mechanically coupled to said transducer for cyclically, at a given repetition rate, oscillating said transducer back and forth about said given axis with a velocity that varies as a predetermined smooth continuous function of time between respective first and second angular limits, said given repetition rate being at least one-hundred cycles per minute.

2. The system defined in claim 1, wherein said second means oscillates said transducer about said given axis with a velocity that varies as a sinusoidal function of time.

3. The system defined in claim 2, wherein said given repetition rate is in the range of one-hundred to fifteen hundred cycles per minute.

4. The system defined in claim 3, wherein said given repetition rate is in the order of three-hundred cycles per minute.

5. The system defined in claim 3, wherein said given repetition rate is in the order of one-thousand cycles per minute.

6. The system defined in claim 1, further includes third means coupled between said second and first means for applying an ultrasonic frequency pulse to said transducer at each of a first set of predetermined angular positions of said transducer during odd half-cycles of oscillation of said transducer and at each of a second set of predetermined angular positions of said transducer during even half-cycles of oscillation of said transducer.

7. The system defined in claim 6, wherein said predetermined angular positions of said first set are interleaved with said predetermined angular positions of said second set.

8. The system defined in claim 7, wherein the angular increment between each pair of successive angular positions of said first set and the angular increment between each pair of successive angular positions of said second set all have substantially the same given value, and respective angular positions of said second set each being situated substantially half way between each pair of successive angular positions of said first set.

9. The system defined in claim 7, further comprising fourth means coupled to said third means for deriving a scan position signal in accordance with the respective values of said predetermined angular positions of said first set and of said second set.

* * * * *